(12) United States Patent
Palma et al.

(10) Patent No.: US 10,430,984 B2
(45) Date of Patent: Oct. 1, 2019

(54) FUSED SLICE OR CINE-LOOP IMAGE FOR MULTI-MODE DBT ACQUISITIONS

(71) Applicant: General Electric Company, Schenectady, NY (US)

(72) Inventors: Giovanni Palma, Yvelines (FR); Pablo Milioni De Carvalho, Yvelines (FR); Ann-Katherine Carton, Yvelines (FR); Razvan Iordache, Yvelines (FR); Serge Muller, Yvelines (FR)

(73) Assignee: General Electric Company, Schenectady, NY (US)

( * ) Notice: Subject to any disclaimer, the term of this patent is extended or adjusted under 35 U.S.C. 154(b) by 215 days.

(21) Appl. No.: 15/381,704

(22) Filed: Dec. 16, 2016

(65) Prior Publication Data

US 2018/0174341 A1 Jun. 21, 2018

(51) Int. Cl.

| G06T 11/60 | (2006.01) |
|---|---|
| A61B 6/00 | (2006.01) |
| A61B 8/08 | (2006.01) |
| A61B 8/00 | (2006.01) |
| G06T 19/20 | (2011.01) |
| A61B 6/02 | (2006.01) |
| A61B 90/00 | (2016.01) |
| A61B 6/04 | (2006.01) |

(52) U.S. Cl.
CPC .............. *G06T 11/60* (2013.01); *A61B 6/463* (2013.01); *A61B 6/469* (2013.01); *A61B 6/502* (2013.01); *A61B 6/5235* (2013.01); *A61B 6/5247* (2013.01); *A61B 8/0825* (2013.01); *A61B 8/463* (2013.01); *A61B 8/469* (2013.01); *A61B 8/5261* (2013.01); *G06T 19/20* (2013.01); *A61B 6/025* (2013.01); *A61B 6/0414* (2013.01); *A61B 6/481* (2013.01); *A61B 6/482* (2013.01); *A61B 6/5241* (2013.01); *A61B 8/403* (2013.01); *A61B 8/5253* (2013.01); *A61B 2090/364* (2016.02); *A61B 2090/376* (2016.02); *G06T 2210/41* (2013.01); *G06T 2219/2016* (2013.01)

(58) Field of Classification Search
None
See application file for complete search history.

(56) References Cited

U.S. PATENT DOCUMENTS

| 8,958,527 | B2 * | 2/2015 | Muller | ................ | A61B 6/025 378/37 |
|---|---|---|---|---|---|
| 2004/0096088 | A1 * | 5/2004 | Kohle | .................... | G06T 15/00 382/128 |

(Continued)

*Primary Examiner* — Tahmina N Ansari
(74) *Attorney, Agent, or Firm* — Boyle Fredrickson, S.C.

(57) ABSTRACT

In the present invention, an image review method and system for performing the method is provided to facilitate the review of image volumes obtained in different imaging modalities and to evaluate the correlation between findings in the respective volumes in an easy to review manner compared with prior art systems and processes. The method and system of the invention provides simulated or actual combined or fused images or representations of registered images obtained in each imaging modality to simplify and accelerate the review of multi-modal breast imaging volumes, in particular when correlation of information between the two modes, including but not limited to, LE and DE, DBT and ABUS, DE and ABUS, etc., is important to evaluate.

24 Claims, 7 Drawing Sheets

(56) References Cited

U.S. PATENT DOCUMENTS

| | | | |
|---|---|---|---|
| 2012/0238870 A1* | 9/2012 | Smith | A61B 6/025 600/431 |
| 2014/0044336 A1 | 2/2014 | Heinlein et al. | |
| 2014/0112563 A1* | 4/2014 | Ruth | G06K 9/4638 382/131 |
| 2014/0328450 A1* | 11/2014 | Pal | G01N 23/046 378/5 |
| 2016/0235380 A1* | 8/2016 | Smith | A61B 6/025 |
| 2017/0332992 A1* | 11/2017 | Liphardt | A61B 6/4494 |
| 2018/0109698 A1* | 4/2018 | Ramsay | G06T 7/11 |
| 2018/0174294 A1* | 6/2018 | Palma | G06T 7/0014 |
| 2018/0174341 A1* | 6/2018 | Palma | G06T 11/60 |

\* cited by examiner

FUSED SLICE OR CINE-LOOP IMAGE FOR MULTI-MODE DBT ACQUISITIONS

FIELD OF THE INVENTION

The invention relates generally to diagnostic mammography procedures utilizing radiological images and more specifically to methods of review of first and second radiological images in conjunction with one another for diagnosing patient conditions.

BACKGROUND OF INVENTION

In digital mammography, radiological images in the shape of mammograms are recorded using an X-Ray imaging apparatus. Herein, typically, for diagnosing such images by a physician multiple images are displayed on a display unit such that the physician can compare the images with one another. For example, the physician can compare current images with images of a prior examination or can view images of a left and a right breast for the purpose of a symmetry comparison.

In contrast-enhanced digital breast tomosynthesis (CE-DBT), the radiologist reviews both dual energy (DE/iodine) and low energy (LE) volumes to perform the diagnostic analysis. In doing so, correlating LE (morphological) structures and DE (contrast uptake/function) structures between the image volumes is important for the reader/radiologist.

Currently the tools available for the review of DE and LE images in CE-DBT are side-by-side (synchronous) review of the images in each volume or toggling between the corresponding images of the 2 volumes. Consequently, reviewing both LE and DE/iodine volumes and correlating the findings therein requires multiple user actions and time. Further, a comparison of the DE and LE radiological images on a screen of a display unit requires a rather large screen because multiple images must be shown side by side on the screen. If images are shown side by side on a screen, in addition it may be hard for a physician to visually establish corresponding locations within images such that a diagnosing may be cumbersome and requires a high level of concentration of the physician.

Because comparing images arranged side by side on a screen of a display unit requires significant time and consideration by the physician to complete the review of the images, there is a need for tools that allow an easy review and diagnosis of different images while at the same time being easy to handle and intuitive to use for a physician.

BRIEF DESCRIPTION OF THE INVENTION

The above-mentioned drawbacks and needs are addressed by the embodiments described herein in the following description.

According to one aspect of an exemplary embodiment of the invention, an image review method and system for performing the method is provided to facilitate the review of image volumes obtained in different imaging modalities and to evaluate the correlation between findings in the respective volumes in an easy to review manner compared with prior art systems and processes. The method and system of the invention simplifies and accelerates the review of multi-modal breast imaging volumes, in particular when correlation of information between the two modes, including but not limited to, LE and DE, DBT and ABUS, DE and ABUS, etc., is important to evaluate. To perform the review, in the method and system for performing the method includes the steps of:

Step 1: Obtaining both a first image volume and a second image volume that are in registry with one another Step 2: Partitioning the first image volume and the image volume into slices numbered 1, 2, . . . i, that are in registry with one another Step 3, Displaying the registered slices of the first and second image volumes in an fused manner.

In one exemplary embodiment, to display registered slices in a fused manner, the slices (1, 2, . . . i) of the first image volume (V1) and the second image volume (V2) can be fused without being combined in a either a single slice view or a cine-loop/scroll of multiple slices where the registered slices of the two image volumes are displayed interleaved as the user moves through the volumes (V1_slice_1 <-> V2_slice_1)-> (V1_slice_2 <-> V2_slice_2)->, etc. For the display of the images for a given slice, when the user is reviewing a selected slice, the registered slice images from the respective volumes, such as V1 slice 1 and V2 slice 1, are displayed in an alternating manner, where the images V1 slice 1 and V2 slice 1 are constantly replaced with one another on the display at a given frequency, to provide the images V1 slice 1 and V2 slice 1 to the user as a single viewable image, with the information from both images being viewable in the displayed image as a result of the switching frequency or flicker rate of the image switching.

According to still another aspect of an exemplary embodiment of the invention, to display registered slices in a fused manner, the slices (1, 2, . . . i) of the first image volume (V1) and the second image volume (V2) can be fused by partitioning the registered images from the respective volumes, such as V1 slice 1 and V2 slice 1 into patches, where the size of an individual patch is an integer multiple of the size of pixel size of V1 slice 1 and V2 slice 1. To form the fused slice image, the content of a patch from fused slice image is copied either from the same location (patch) of V1 slice 1 or V2 slice 1 image, following the pattern of a checkerboard such that the fused slice image is formed from a patterned arrangement of the patches obtained from each of the V1 slice 1 and V2 slice 1 images.

According to another aspect of an exemplary embodiment of the invention, to display registered slices in a fused manner, the fused slice image is obtained from the V1 slice 1 and V2 slice 1 images, using either the method of the first or second embodiment. The fused slice image is obtained by color coding the V1 slice 1 image into the V2 slice 1 images, such as, for example, adding different colors to V1 slice 1 image and the V2 slice 1 images, thereby color coding the information being displayed from each of the V1 slice 1 image into the V2 slice 1 images in the fused slice image.

According to still another aspect of an exemplary embodiment of the invention, to display registered slices in a fused manner, the fused slice image is obtained by selecting a point on cross-fading transition curve between the V1 slices and V2 slices using a suitable controller or input to the system, whereby the image provided by the fused slice is weighted towards the V1 slice or V2 slice registered with one another at the selected height and being displayed by selecting the desired point on the curve to provide the selected combination of the V1 and V2 slice images. This can be accomplished in multiple manners such as by altering the flicker rate of the slice images with regard to one another, such that the images displayed for a fused slice illustrate one of the particular V1 slice or the particular V2 slice more prominently or frequently, depending upon the cross-fade/weights selected for the respective V1 and V2 slice images.

According to still a further aspect of one exemplary embodiment of the invention, to display registered slices in a fused manner, a fused slice image is obtained from a V1 slice and V2 slice registered with one another at the selected height using either the method of the first or second embodiment. The fused slice image is obtained by color coding the V1 slice and/or the V2 slice relative to one another and partitioning the fused slice into patches, e.g., four rectangular patches for the display image with the patches located in the upper left—UL, upper right—UR, lower left—LL, lower right—LR sections of the fused slice image. The content of patches UL and LR are copied from the same location (patch) of either the V1 slice or the V2 slice and the content of patches UR and LL are copied from the same location (patch) of the opposite slice. In the fused slice image, the size of the patches can be dynamically adjusted by the user by moving the point of intersection of the patches, e.g., the center of the fused slice image, anywhere in the image to shift the content of the fused image slice to display more or less of the V1 slice or the V2 slice.

According to still a further aspect of one exemplary embodiment of the invention, a method for combining a first radiological image from a first image volume and a second radiological image from a second image volume to form a fused image includes the steps of obtaining a first image volume utilizing a first imaging system modality, obtaining a second image volume that is in registry with the first image volume utilizing a second imaging system modality, partitioning the first image volume into a number of first images at selected heights within the first image volume and the second image volume into a number of second images at selected heights within the second image volume, with the second images in registration with the first images and combining portions of at least one first image and at least one second image into the fused image.

According to still a further aspect of one exemplary embodiment of the invention, a method for displaying a first radiological image from a first image volume and a second radiological image from a second image volume to form a fused representation includes the steps of obtaining a first image volume utilizing a first imaging system modality, obtaining a second image volume that is in registry with the first image volume utilizing a second imaging system modality, partitioning the first image volume into a number of first images within the first image volume and the second image volume into a number of second images within the second image volume, with the second images in registration with the first images and alternating the display of at least one first image and at least one second image to form the fused representation.

According to still a further aspect of one exemplary embodiment of the invention, an imaging system for obtaining a first image volume in a first imaging modality and a second image volume in registration with the first image volume in a second modality in order to combine at least one first image from the first image volume with at least one second image form the second image volume to form one or more fused images includes an X-ray source, an X-ray detector capable of detecting X-rays emitted from the X-ray source, a system controller operably connected to the X-ray source to control the operation and position of the X-ray source, an image processing module operably connected to the system controller and to the X-ray source, the image processing module configured to process image data from the X-ray detector forming the first image volume and the second image volume, an operator interface connected to the image processing module to selected images from the first image volume and the second image volume to be combined into the fused images and to select the mode of combination of the images and a display operably connected to the image processing module to display the fused images.

According to still a further aspect of one exemplary embodiment of the invention, an imaging review system for obtaining a first image volume in a first imaging modality and a second image volume in registration with the first image volume in a second modality in order to combine at least one first image from the first image volume with at least one second image form the second image volume to form one or more fused representations or images includes an image processing module adapted to receive image data from a system controller of an imaging device, the image processing module configured to process the image data from the X-ray detector forming the first image volume and the second image volume, an operator interface connected to the image processing module to selected images from the first image volume and the second image volume to be combined into the fused images and to select the mode of combination of the images and a display operably connected to the image processing module to display the fused images.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
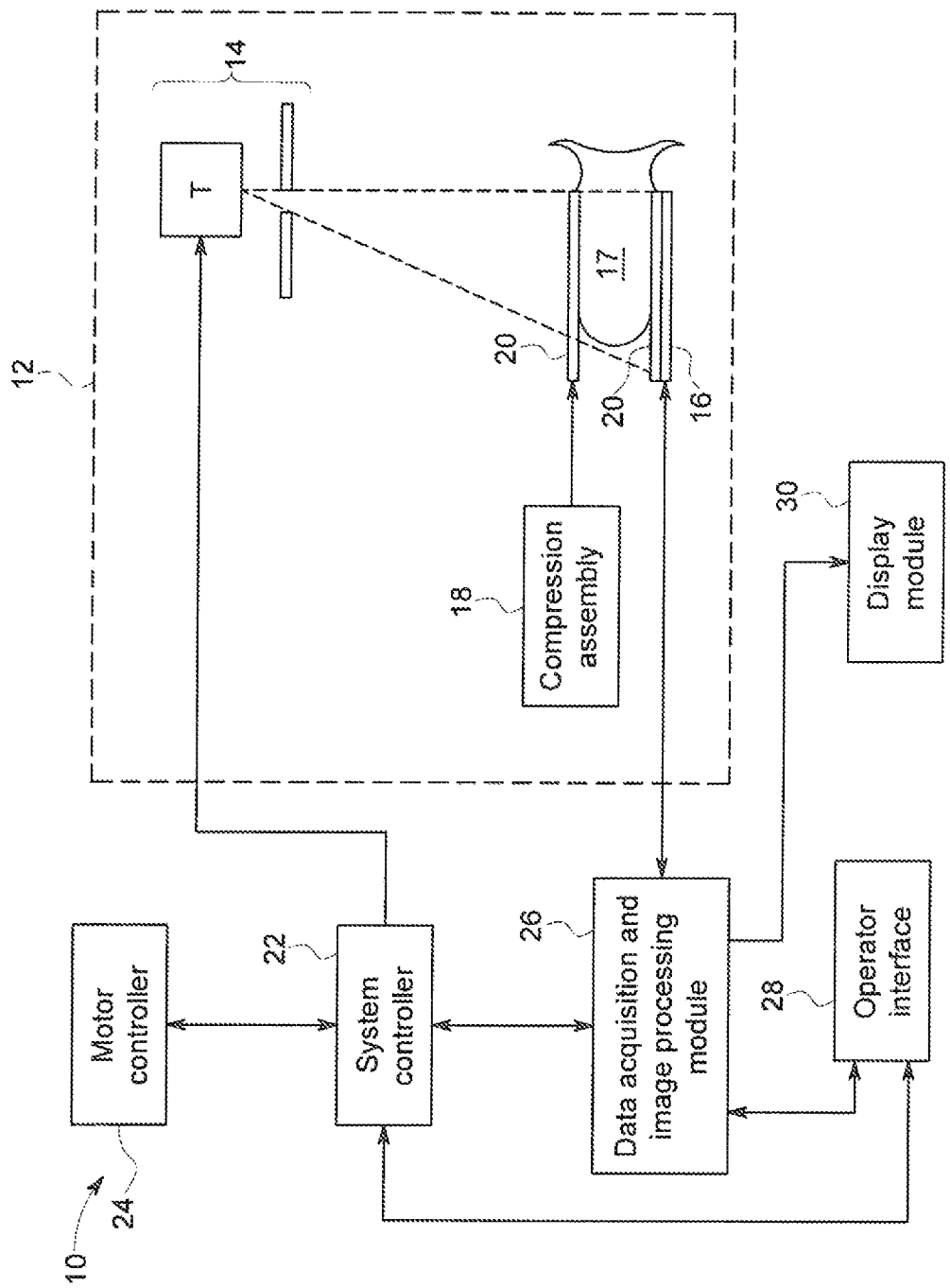
FIG. 1 is a diagrammatic representation of a mammography imaging system according to one exemplary embodiment of the invention.

Referring first to FIG. 1, an exemplary tomosynthesis imaging system 10 for use in accordance with the present approach is illustrated diagrammatically. As depicted, the tomosynthesis imaging system 10 includes an image data acquisition system 12. The image data acquisition system 12 includes an X-ray source 14, an X-ray detector 16 and a compression assembly 18. The tomosynthesis imaging system 10 further includes a system controller 22, a motor controller 24, data acquisition and image-processing module 26, an operator interface 28 and a display module 30.

The X-ray source 14 further includes an X-ray tube and a collimator configured to generate a beam of X-rays when activated. The X-ray tube is one example of the X-ray source 14. Other types of the X-ray sources 14 may include solid state X-ray sources having one or more emitters. The X-ray source 14 may be movable in one, two or three dimensions, either by manual or by automated means. The image data acquisition system 12 may move the X-ray source 14 via tracks, ball-screws, gears, belts, and so forth. For example, the X-ray source 14 may be located at an end of a mechanical support, such as a rotating arm or otherwise adjustable support, which may be moved by the image data acquisition system 12 or by an operator. Instead of, or in combination with, a mechanical displacement of the X-ray source 14, different view angles may be achieved through individually addressable source points.

The X-ray detector 16 may be stationary, or may be configured to move either independently or in synchrony with the X-ray source 14. In a present embodiment, the X-ray detector 16 is a digital flat panel detector. The image data acquisition system 12 may move the X-ray detector 16, if mobile, via tracks, ball-screws, gears, belts, and so forth. In one embodiment, the X-ray detector 16 also provides support for an object, such as a breast 17 of a patient to be imaged, thereby forming one part of the compression assembly 18. In other embodiments, the X-ray detector may be disposed immediately or proximately beneath a bottom plate of compression assembly 18, i.e., in such an embodiment, the breast 17 does not rest directly on the detector 16 but on a plate or other compressing support above the detector 16.

The compression assembly 18, whether including two compression plates or a compression plate and the detector 16, is configured to compress the patient breast 17 for performing tomosynthesis imaging and to stabilize the breast 17 during the imaging process to minimize patient motion while data is acquired. In one embodiment, the breast is compressed to near uniform thickness. In the depicted embodiment, the compression assembly 18 includes at least one mammography compression plate 20, which may be a flat, inflexible plate, deformable sheet, or alternative compression device. In one embodiment, the mammography compression plate 20 is configured to be radiolucent to transmit X-rays and is further configured to be sonolucent to transmit ultrasound signals. The compression assembly 18 may be used to stabilize the imaged breast 17 during acquisition of both the tomosynthesis and the ultrasound datasets, thereby enabling the acquisition of co-registered tomosynthesis X-ray images, ultrasound images, and Doppler images.

The system controller 22 controls operation of the image data acquisition system 12 and provides for any physical motion of the X-ray source 14 and/or the X-ray detector 16. In the depicted embodiment, movement is, in turn, controlled through the motor controller 24 in accordance with an imaging trajectory for use in tomosynthesis. Therefore, by means of the image data acquisition system 12, the system controller 22 may facilitate acquisition of radiographic projections at various angles relative to a patient. The system controller 22 further controls an activation and operation of other components of the system, including collimation of the X-ray source 14. Moreover, the system controller 22 may be configured to provide power and timing signals to the X-ray source 14. The system controller 22 may also execute various signal processing and filtration functions. In general, the system controller 22 commands operation of the tomosynthesis imaging system 10 to execute examination protocols and to acquire resulting data.

For example, in the depicted embodiment of FIG. 1, the system controller 22 controls a tomosynthesis data acquisition and image-processing module 26. The tomosynthesis data acquisition and image-processing module 26 communicates with the X-ray detector 16 and typically receives data from the X-ray detector 16, such as a plurality of sampled analog signals or digitized signals resulting from exposure of the X-ray detector to X-rays. The tomosynthesis data acquisition and image-processing module 26 may convert the data to digital signals suitable for processing and/or may process sampled digital and/or analog signals to generate volumetric images of the breast 17 using one or more modalities of the imaging system 10, such as a low energy (LE) imaging modality to obtain a LE image volume and a dual energy (DE/iodine) imaging modality to obtain a DE/iodine image volume using a contrast-enhanced digital breast tomosynthesis (CE-DBT) procedure.

The operator interface 28 may include a keyboard, a mouse, and other user interaction devices. The operator interface 28 can be used to customize settings for the tomosynthesis imaging and for effecting system level configuration changes as well as for allowing operator activation and operation of the tomosynthesis imaging system 10. In the depicted embodiment, the operator interface 28 is connected to the tomosynthesis data acquisition and image-processing module 26, the system controller 22 and the display module 30. The display module 30 presents a reconstructed image of an object, or of a region of interest within the object, based on data from the data acquisition and image-processing module 26. As will be appreciated by those skilled in the art, digitized data representative of individual picture elements or pixels is processed by the tomosynthesis data acquisition and image-processing module 26 to reconstruct the desired image. The image data, in either raw or processed forms, may be stored in the system or remotely for later reference and image reconstruction.

Figure 2:
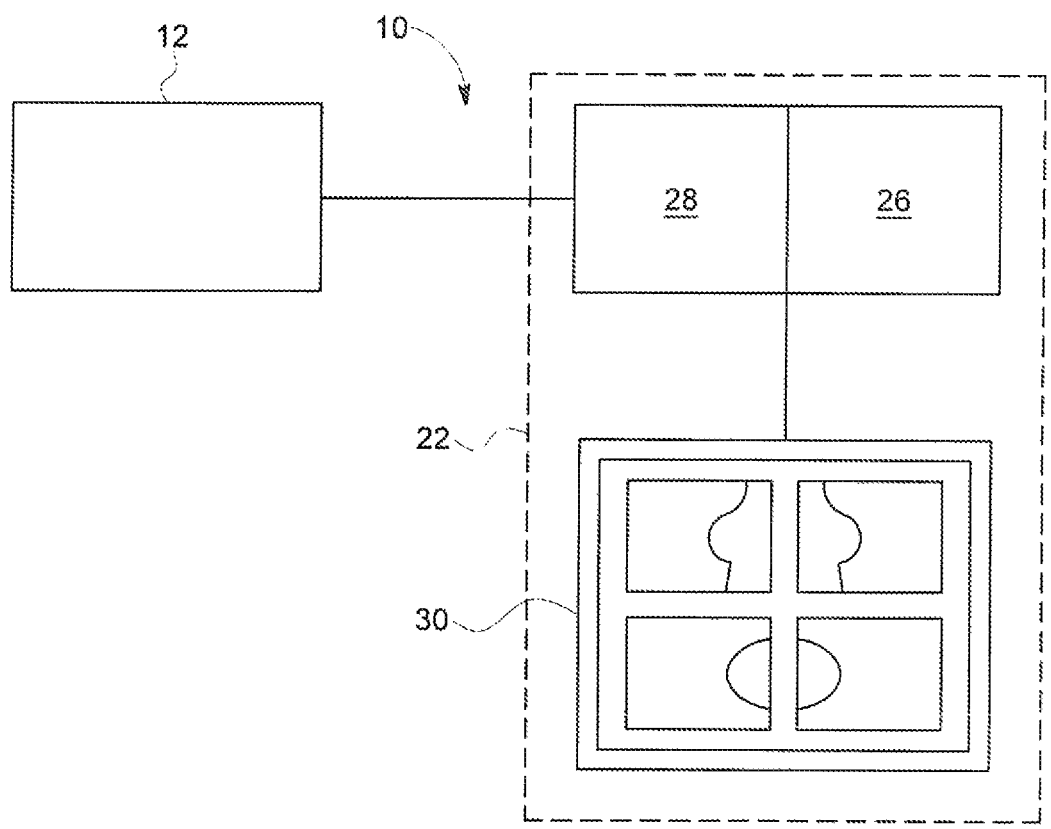
FIG. 2 shows a schematic drawing of an arrangement of an imaging apparatus in conjunction with an image processing apparatus according to one exemplary embodiment of the invention.

FIG. 2 shows a simplified schematic view the imaging system 10 for conducting a mammography (DBT) examination. Herein, image data acquisition system 12 is connected to the system controller/processing unit 22 including the image processing apparatus 26, the operator interface 28 and the display module 30. In this arrangement, the X-Ray images of a female breast are recorded and provided to the processing unit 22 for image processing of the images. The processing unit 22 forms the images into volumes that are comprised of numerous slice images identified at various heights within the image volume. The slice images can be selected and illustrated on the display unit 30 in accordance with one or more embodiment of the invention for diagnosis by a physician.

Figure 3:
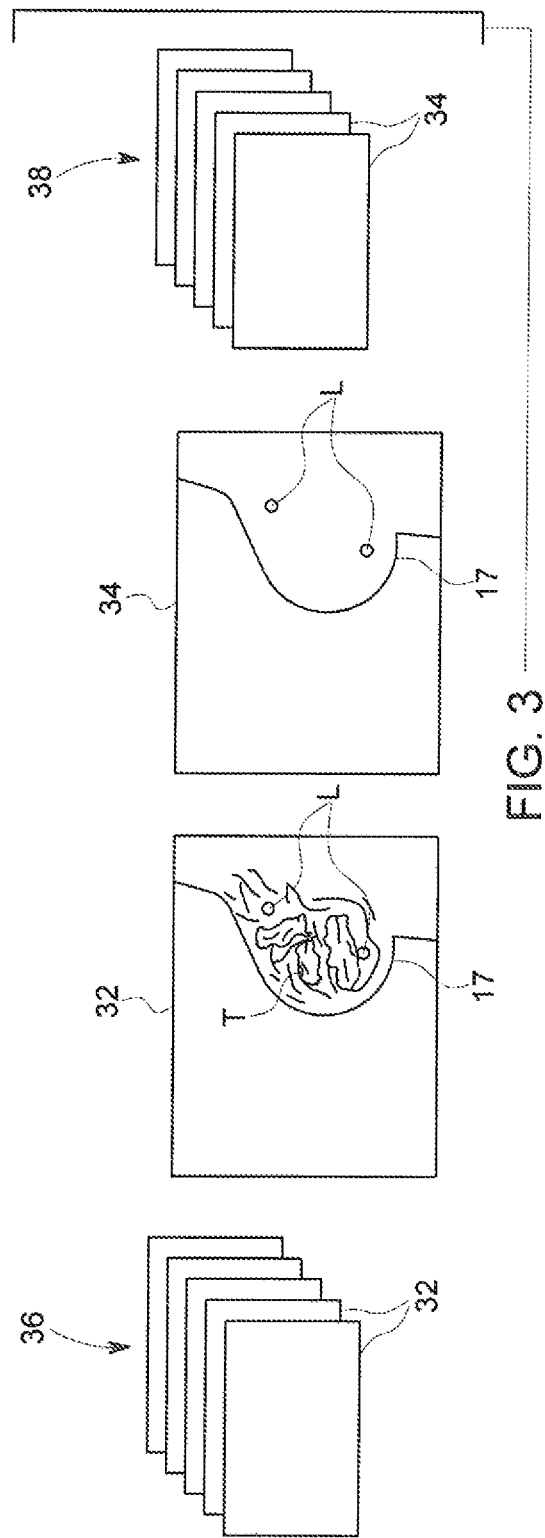
FIG. 3 shows different radiological images showing the same object and being co-registered according to an exemplary embodiment of the invention.

Referring now to FIG. 3, the imaging system 10 is operated to obtain images of the breast 17 in two different modalities. These modalities can include, but are not limited to, low energy (LE), dual energy (DE), such as used in CE-DBT, contrast-enhanced spectral mammography (CESM) and automated breast ultrasound (ABUS) modalities, among others. In the illustrated exemplary embodiment in FIG. 3, the images shown are taken using in a first imaging modality, such as a LE imaging modality, providing a first image 32, such as an LE image 32, and a second imaging modality, such as a DE imaging modality, providing a second image 34, such as a DE image 34. The various first and second images 32,34 obtained in each modality are processed and formed by the processing unit 22 into respective first image volume 36 and second image volume 38, such as LE and DE image volumes. The LE and DE images 32,34 obtained in the different modalities can provide varying information to the physician, such as morphological structures in LE images 32 and contrast uptake/function structures in DE images 34, for example. Dependent on the type of image, different structures, including tissue T and lesions L, in the breast or object 17, are visualized differently in the radiological LE and DE images 32,34. The LE and DE images 32,34, however, are taken in the same examination without moving the X-ray source 14, compression assembly 18 and object 17 such that the LE and DE images 32,34 and corresponding volumes 36,38 are registered with one another, i.e. they use the same coordinate system and show identical structures at the same locations.

In order to facilitate a comparative diagnosis of the different radiological images, e.g., LE images 32 and DE images 34, the review of the images 32,34 is performed by fusing the images 32,34 with one another to provide a single image at each location or slice selected in the respective image volumes 36,38 that provides the information of the registered images 32,34 at that location in each volume 36,38.

Figure 4:
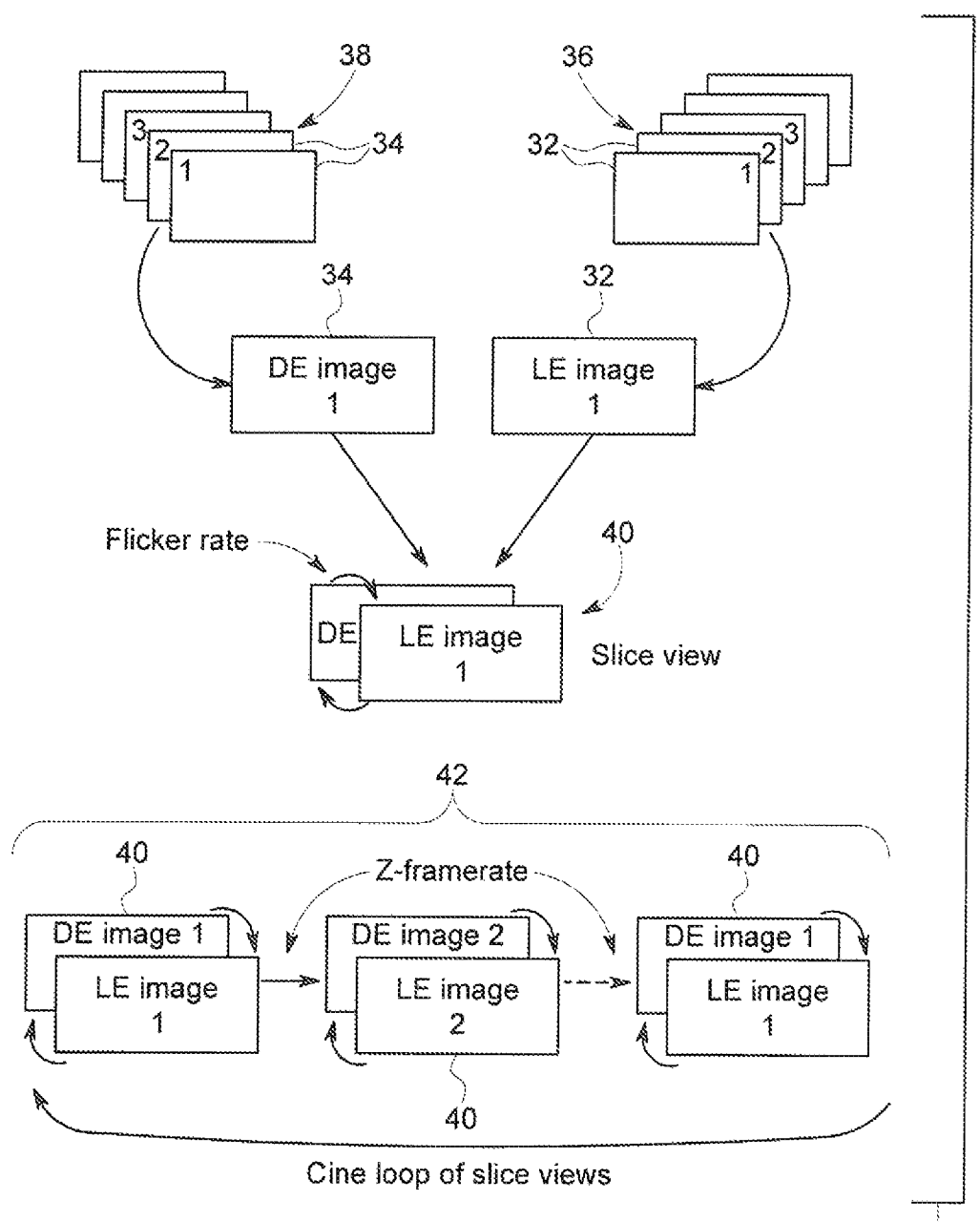
FIG. 4 is a schematic view of a sequence of forming a fused slice image and displaying the fused slice image in a slice view or cine-loop of multiple slice views according to one exemplary embodiment of the invention.

Referring now to FIG. 4, in a first illustrated exemplary and non-limiting embodiment of the invention, a method of operating the imaging system 10 to obtain images of the object or breast 17 includes the step of:

Step 1: Obtaining both an LE image volume 36 and a DE image volume 38 that are in registry with one another;

Step 2: Partitioning the LE volume 36 and the DE volume 38 into a number of slice images 32,34, respectively, that are in registry with one another; and Step 3: Displaying the registered slices 32,34 of the LE and DE volumes 36,38 in a fused manner.

With regard to step 3, in one exemplary and non-limiting embodiment of the invention, the when a user desires to view one or more of the LE slices 32 and the DE slices 34 that are registered with one another, i.e., that are located at the same height, width, etc. within the respective image volumes 36,38, the slices 32,34 can be fused by interleaving the registered LE slice(s) 32 and the DE slice(s) 34 with one another. With regard to the display of an individual pair of images, i.e., a LE slice 32 and a DE slice 34, this involves obtaining the LE slice 32 and DE slice 34 for the desired or selected location in the volumes 36,38, and operating the display 30 to show the LE slice 32 and the DE slice 34 in an alternating manner.

The framerate or frequency of switching between LE slice 32 and DE slice 34 at the selected slice or height (1, 2, 3, . . . , i) within the volumes 36,38, the speed of switching between individual pairs of slices or images 32,34 at a particular height (1, 2, 3, . . . , i) within the volumes 36,38 is designated the flicker rate. The flicker rate can be adjusted to vary the rate at which the LE slice 32 and DE slice 34 are alternated, and gives the user impression that that the information of both LE slice 32 and DE slice 34 at the selected slice or height (1, 2, 3, . . . , i) has been combined into a single fused slice 40, but without any actual combination of the information or images forming the LE slice 32 and the DE slice 34 with one another.

In addition, other than viewing a single fused image 40 of the LE slice 32 and the DE slice 34 at a selected slice or height (1, 2, 3, . . . , i) within the volumes 36,38, the user can operate the system controller/processing unit 22, such as through the user/operator interface 28, to provide a view on the display unit 30 of multiple slices or heights (1, 2, 3, . . . , i) within the volumes 36,38, or the entire volume 36/38. This display provides a cine-loop or scroll image 42 where the pairs of images or slices 32,34 of the volumes 36,38 registered with one another at each slice/height (1, 2, 3, . . . , i) are each displayed as interleaved fused images 40 as the user moves through the volumes 36,38. In the cine loop or scrolling display format, the framerate of switching between registered pairs of images or slices 32,34 at different and/or adjacent heights, e.g., slice 1 and slice 2, is called the Z-framerate. The Z-framerate is directly imposed by user to view fused images 40 at different heights when in a scrolling mode, such as by the operation of a suitable scrolling controller as the user moves through the various slices in the volumes 36,38. Alternatively, in a cine mode the Z-framerate can be adjusted and/or preset by user where multiple fused images 40 for the slices (1, 2, 3, . . . , i) in the volumes 36,38 are shown in a cine-loop of the selected slices or of the entire volume 36,38.

Figure 5:
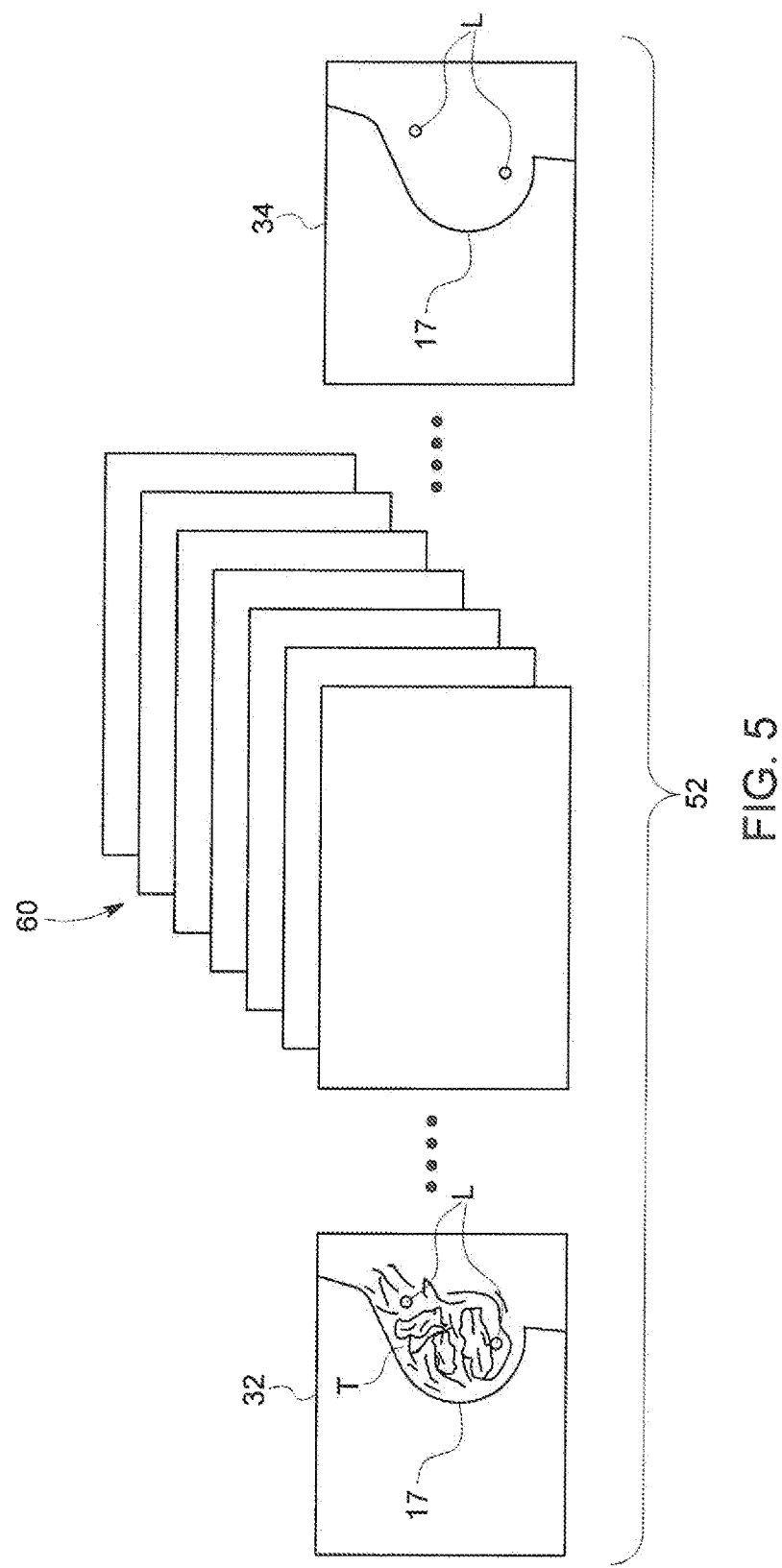
FIG. 5 shows a schematic view of a sequence comprising a first radiological image, a series of intermediate images formed as interpolations between the first radiological image and a second radiological image, and the second radiological image according to one exemplary embodiment of the invention.

In another exemplary and non-limiting embodiment of the invention illustrated in FIG. 5, the slices 32,34 can be combined to form a number of intermediate images 60 that are weighted towards the display of information from either the LE image 32 or the DE image 34 over the remaining image 32,34. While any suitable weighting factor or method can be employed, one exemplary system and method is disclosed in US Patent Application Publication No. 2014/0044336, entitled *Method And Apparatus For Displaying Radiographical Images*, which is expressly incorporated herein in its entirety by reference for all purposes. In this method, the intermediate image or images 60 between the first radiological image 32 and the second radiological image 34 are determined as interpolations between the first radiological image 32 and the second radiological image 34. Each interpolation herein may be a linear combination of the first radiological image 32 and the second radiological image 34, hence, providing a linear transition from the first radiological image 32 to the second radiological image 34 and vice versa. By means of the sequence of intermediate images 60 the one radiological image 32,34 is sequentially faded in while the other one 32,34 fades out such that a transition or sequence 62 from one image 32,34 to the other 32,34 via the intermediate images 60 is provided at a framerate or flicker rate for switching between the respective images 32,34,60 that is either manually or automatically determined.

For computing the interpolation, a continuous transitional function may be used. Such transitional function may be computed as a progressing transition solely depending on the number of the intermediate image in between the first radiological image 32 and the second radiological image 34. The transitional function however may also take further parameters into account such as a local intensity or specific contents of the radiological images 32,34 such that a content dependent transition is provided.

In particular the interpolation may be computed based on specific regions or structures contained in at least one of the first radiological image 32 and the second radiological image 34 such that a fading effect is achieved only within a specific region or for a specific structure. Or the interpolation may be computed based on a local intensity value of at least one of the first radiological image 32 and the second radiological image 34 such that the interpolation depends on the image intensity at the respective pixel locations.

In principle, two approaches of computing the series of intermediate images 60 are possible. First, the intermediate images 60 can be computed on the fly upon a specific viewing request of a user. Hence, when a user selects to view a cross-fading from one radiological image 32,34 to another 32,34, the series of images 60 is computed on the fly and the cross-fading sequence is shown to the user. The intermediate images 60 may then be stored for a repeated viewing of the cross-fading sequence, or the intermediate images 60 may not be stored requiring for a repeated computation if the cross-fading sequence shall be viewed again. Second, the intermediate images 60 could be pre-computed in a pre-processing step and stored in memory such that the complete sequence of images is available already upon request by a user. With this approach the computational burden is shifted to a pre-processing step hence reducing the computational load upon a viewing request by a user.

The intermediate images 60 can also serve to provide a cross-fading sequence generating a cinematic transition from one radiological image 32,34 to the other 32,34. In principle, a transition between more than two radiological images 32,34 can be provided, wherein a first sequence of images providing a transition from a first radiological image 32 to a second radiological image 34 may be concatenated with a second sequence of images providing a transition from the second radiological image to a third radiological image and so on. In this way, multiple sequences of images can be combined by concatenation, hence providing a cinematic transition between multiple radiological images, for example multiple slabs of a three-dimensional imaging volume 36, 38.

Figure 6:
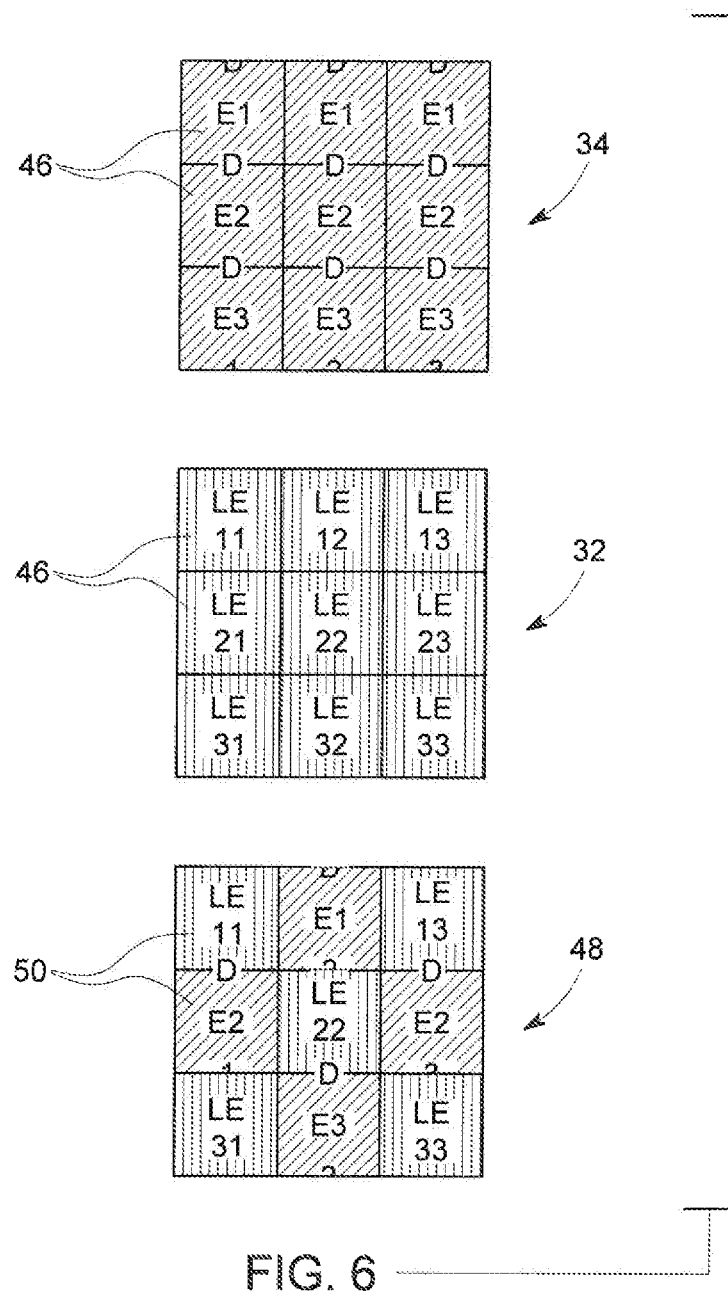
FIG. 6 shows a schematic view of a sequence of forming a fused slice image and displaying the fused slice image according to another exemplary embodiment of the invention.

Referring now to FIG. 6, in another exemplary and non-limiting embodiment of the invention, step 3 of the method can be performed by combining the LE image 32 and DE image 34 with one another to form a fused image 48 for a particular slice or height (1, 2, 3, . . . , i) in the volumes 36,38. To form the fused image 48, the LE image 32 and the DE image 34 are partitioned into patches 46, where the size of an individual patch 46 is selected to be an integer multiple of the size of pixel sizes of the LE image 32 and the DE image 34. The content of a patch 50 within the fused image 48 is copied either from the same location patch 46 of the LE image 32 or DE image 34 in order to provide the desired representation of the information from the LE image 32 and the DE image 34 in the fused image 48. For example, as shown in the illustrated exemplary embodiment in FIG. 5, the copying of patches 48 from LE image 32 and DE image 34 can follow the pattern of a chessboard, with adjacent patches 50 being copied from different images 32,34. In this manner, the fused image 48 is formed of the patches 46 of images 32,34 copied in the desired manner into patches 50 to form the fused image 48. In addition, the size of the patches 46,50 may be user adjustable or may adjusted as a function of frame rate of the display of the fused images 48 in order to optimize the impression of fusion of information between the slice images 32,34 of the volumes 36,38 utilized to form individual fused slice 48. For example, the first and second patches 46,50 utilized to form a first fused image 48 can be altered in size to form altered third and fourth patches (not shown) enable the formation of a second fused image 48 that is different in configuration from the first fused image 48 and/or multiple intermediate fused images (not shown), such as between first image 32 and second image 34.

In another exemplary and non-limiting embodiment of the invention, when performing step 3, in any of the prior embodiments one or both of the LE image 32 and the DE image 34 is color coded, i.e., provided with a color for the image 32,34 different from the other image 32,34. In this manner, in addition to providing a simulated fused image 40 or an actual fused image 48, or an intermediate image 60, the images 40,48,60 are also provided with different colors for coding the information provided by the LE image 32 and the DE image 34 being displayed in the fused image 40,48.

Figure 7:
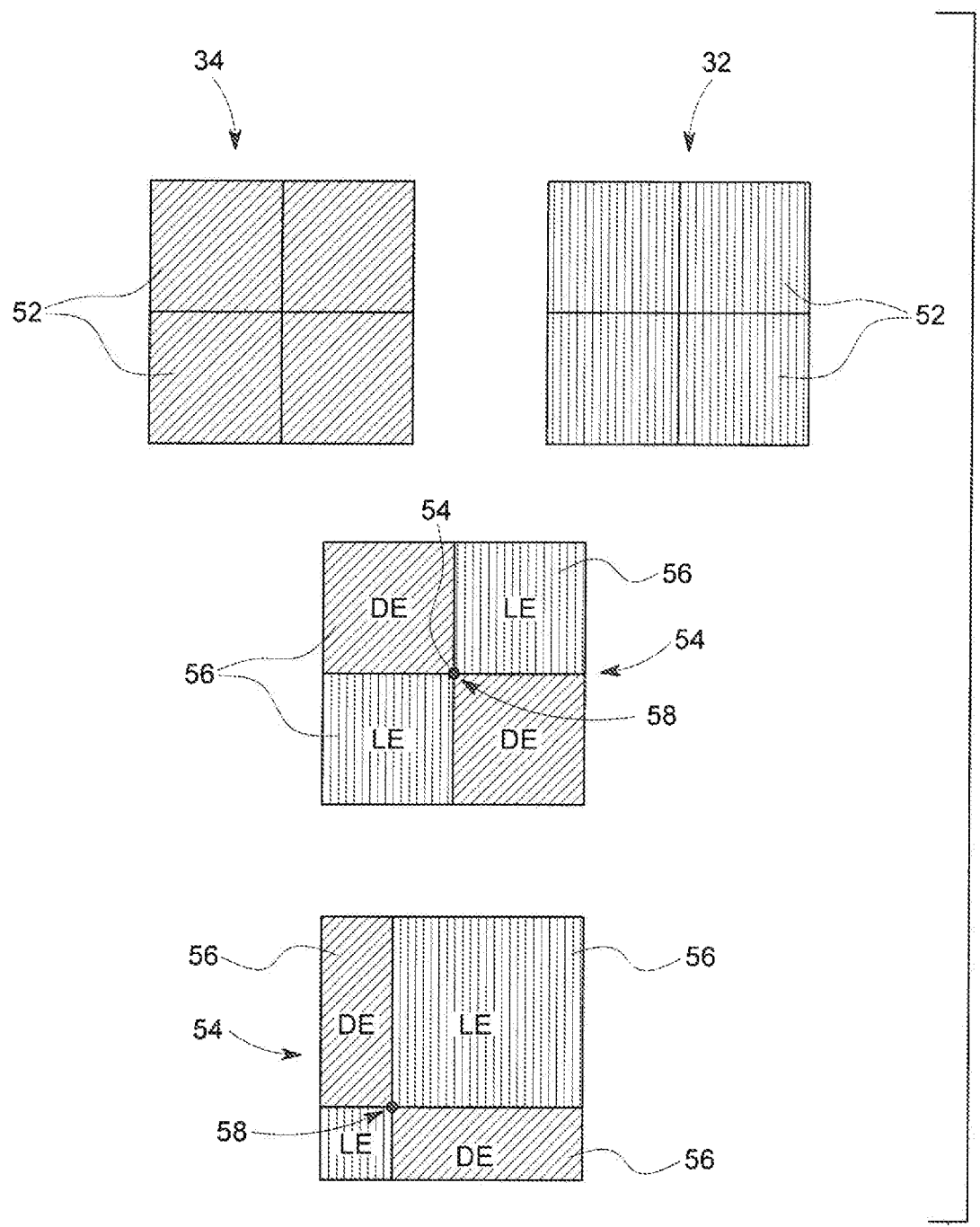
FIG. 7 shows a schematic view of a sequence of forming a fused slice image and displaying the fused slice image according to still another exemplary embodiment of the invention.

Referring now to FIG. 7, in still a further exemplary and non-limiting embodiment of the invention, the LE image 32 and DE image 34 obtained in the manner of any prior embodiment can be partitioned into patches 52, such as into four (4) rectangular patches 52 located at the upper left—UL, upper right—UR, lower left—LL, lower right—LR quadrants of the LE image 32 and the DE image 34. The fused image 54 is formed by copying the content of certain patches 52 from the LE image 32 or the DE image 34 into patches 56 disposed in the same location of the fused image 54 as the location of either the LE image 32 or the DE image 34 from which the patches 56 were copied. Once formed of the copied patches 56, the fused image 54 is displayed with a weighting factor or an adjustment cursor 58 disposed at the intersection point 64 of the patches 56. The adjustment cursor 58 can be moved across the fused image 54 to dynamically adjust the content of the fused image 54 to display more or less of the various patches 56 of the LE image 32 or DE image 34. The movement of the cursor 58 can adjust the content of the fused image 54 by expanding the selected patch(es) 56 to provide a magnification of the patch(es) 56 or by showing additional information in the expanded area of the patch(es) 56 from the LE image 32 or DE image 34 from which the patch(es) 56 was copied. In still another exemplary embodiment, the fused image or slice 54 can include color coding the patches 56 obtained from the LE image 32 and the DE image 34 relative to one another. Further, the weighting factor or cursor 58 can be used or positioned at different locations on different fused images 54 in order to produce multiple intermediate fused images (not shown), such as between first image 32 and second image 34 or between pairs of images 32,34 in a cine-loop. In addition, multiple weighting factors can be employed to create different fused images 40,48 or intermediate images 60, as necessary.

In other alternative and exemplary, non-limiting embodiments of the invention, in any of the prior embodiments, either the LE volume 36 or DE volume 38, and the images 32,34 contained therein, is replaced by a volume obtained from another imaging modality, such as an ABUS volume, that is registered to the DBT acquisition geometry for combination with either the LE volume 36 or DE volume 38 to obtain the fused images 40,48 or intermediate image 60.

Is still other alternative embodiments, any of the individual fused images 40,48,54,60 formed and described in the previously described embodiments can be combined with other fused images 40,48,54,60, such as using different pairs of registered first images 32 and second images 34, to be utilized in a cine-loop or a scroll through all or selected portions of the image volumes 36,38, such as the pairs of images or slices 32,34 utilized to form those fused images 40,48,54,60. Further, any adjustment features of the individual fused images 40,48,54,60 are available and/or can be employed on the fused images 40,48,54,60 upon stoppage of the cine-loop or scroll to view a particular fused image 40,48,54,60 or used to set parameters for one or more of the fused images 40,48,54,60 as they are consecutively viewed in the cine-loop or scroll.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for displaying a first radiological image from a first image volume and a second radiological image from a second image volume to form a fused representation, the method comprising the steps of:
    obtaining a first image volume utilizing a first imaging system modality;
    obtaining a second image volume that is in registry with the first image volume utilizing a second imaging system modality;
    partitioning the first image volume into a number of first images within the first image volume and the second image volume into a number of second images within the second image volume, with the second images in registration with the first images; and
    continuously alternating the display of at least one first image and at least one second image at a selected frame rate form the fused representation.

2. The method of claim 1, further comprising the step of interpolating at least one first image and at least one second image to form at least one intermediate image, and wherein the step of alternating the display comprises displaying the at least one intermediate image between the at least one first image and the at least one second image.

3. The method of claim 2, wherein the step of alternating the display of at least one of a first image, a second image or an intermediate image comprises altering the framerate of the display of the at least one intermediate image between the at least one first image and the at least one second image.

4. The method of claim 3, wherein the step of altering the framerate of the display is performed manually.

5. The method of claim 1, wherein the step of alternating the display of the at least one first image and the at least one second image comprises the step of displaying a number of registered pairs of first images and second images in an alternating manner without combining the first images and the second images.

6. The method of claim 5, further comprising the step of alternating the display of the number of registered pairs of first images and second images in a scrolling manner.

7. The method of claim 5, further comprising the step of alternating the display of the number of registered pairs of first images and second images in a cine-loop.

8. The method of claim 7, further comprising the step of altering the framerate of the display of the number of registered pairs of first images and second images in the cine-loop.

9. The method of claim 1, further comprising the step of color coding at least one of the at least one first image and the at least one second image.

10. The method of claim 1, wherein the first imaging system modality and the second imaging system modality are each selected from the group consisting of a LE modality, a DE modality, a CESM modality, and an ABUS modality.

11. A method for combining a first radiological image from a first image volume and a second radiological image from a second image volume to form a fused image, the method comprising the steps of:
    obtaining a first image volume utilizing a first imaging system modality;
    obtaining a second image volume that is in registry with the first image volume utilizing a second imaging system modality;
    partitioning the first image volume into a number of first images at selected heights within the first image volume and the second image volume into a number of second images at selected heights within the second image volume, with the second images in registration with the first images; and
    combining non-overlapping portions of at least one first image and at least one second image into the fused image,
wherein the step of combining non-overlapping portions of the at least one first image and the at least one second image comprises the steps of:
    dividing the at least one first image into a number of first patches;
    dividing the at least one second image into a number of second patches in registry with the number of first patches; and
    combining selected non-overlapping first patches and selected second patches to form the fused image.

12. The method of claim 11, wherein the fused image is a first fused image and further comprising the steps of:
    forming the at least one first image into a number of third patches;
    forming the at least one second image into a number of fourth patches; and
    combining selected third patches and selected fourth patches to form a second fused image.

13. The method of claim 11 wherein the step of combining the selected first patches and the selected second patches comprises forming a pattern of first and second patches in the fused image where no first patches are adjacent one another.

14. The method of claim 11 wherein the step of combining the selected first patches and the selected second patches comprises forming a pattern of first and second patches in the fused image where no second patches are adjacent one another.

15. The method of claim 11 further comprising the step of color coding at least one of the selected first patches and the selected second patches prior to combining the selected first patches and selected second patches to form the fused image.

16. The method of claim 11 wherein the step of combining the selected first patches and selected second patches comprises the steps of:

inputting a factor to adjust the number of first patches and second patches combined to form the fused image; and forming the fused image of the adjusted number of first patches and second patches.

17. The method of claim 16, wherein the factor is a weighting factor for each first patch and each second patch to provide blending between the first patch and the second patch within the fused image.

18. The method of claim 17 Wherein the weighting factor comprises a number of weighting factors applied to produce several intermediate images between the first image and the second image.

19. The method of claim 11 further comprising the step of adjusting the size of one or more patches in the fused image after combining the selected first patches and selected second patches to form the fused image.

20. An imaging review system for obtaining a first image volume in a first imaging modality and a second image volume in registration with the first image volume in a second modality in order to combine at least one first image from the first image volume with at least one second image form the second image volume to form one or more fused representations or images, the imaging review system comprising:

an image processor configured to receive image data from a system controller of an imaging device, the image processor configured to process the image data from the X-ray detector forming the first image volume and the second image volume; and an operator interface connected to the image processing module to selected images from the first image volume and the second image volume to be combined into the fused images and to select the mode of combination of the images, wherein the fused images are formed by continuously alternating the display of at least one first image and at least one second image at a selected frame rate to form the fused image, by combining non-overlapping patches of at least one first image and at least one second image to form the fused image, and combinations thereof.

21. The imaging review system of claim 20 further comprising a display operably connected to the image processor to display the fused images.

22. An imaging review system for reviewing a first image volume in a first imaging modality and a second image volume in registration with the first image volume in a second modality in order to display at least one first image from the first image volume with at least one second image form the second image volume to form one or more fused images, the imaging system comprising:

a system controller operably connected to an X-ray source to control the operation and position of the X-ray source;

an image processor operably connected to the system controller and to the X-ray source, the image processor configured to process image data from an X-ray detector forming the first image volume and the second image volume; and an operator interface connected to the image processor to selected images from the first image volume and the second image volume to be combined into the fused images and to select the mode of combination of the images, wherein the fused images are formed by continuously alternating the display of at least one first image and at least one second image at a selected frame rate to form the fused image, by combining non-overlapping patches of at least one first image and at least one second image into the fused image, and combinations thereof.

23. The imaging system of claim 22 wherein the imaging system is configured to operate in a first imaging modality and a second imaging modality that are different from one another.

24. The imaging system of claim 22 further comprising a display operably connected to the image processing module to display the fused images.

* * * * *

UNITED STATES PATENT AND TRADEMARK OFFICE
CERTIFICATE OF CORRECTION

PATENT NO. : 10,430,984 B2
APPLICATION NO. : 15/381704
DATED : October 1, 2019
INVENTOR(S) : Giovanni Palma Page 1 of 1

It is certified that error appears in the above-identified patent and that said Letters Patent is hereby corrected as shown below:

In the Claims

Claim 1, Column 11, Line 42, after "rate" insert -- to --;

Claim 18, Column 13, Line 9, delete "Wherein" and substitute therefor -- wherein --.

Signed and Sealed this
Nineteenth Day of November, 2019

Andrei Iancu
*Director of the United States Patent and Trademark Office*